United States Patent [19]
Bliss et al.

[11] Patent Number: 5,704,890
[45] Date of Patent: Jan. 6, 1998

[54] REAL TIME SENSOR FOR THERAPEUTIC RADIATION DELIVERY

[75] Inventors: Mary Bliss; Richard A. Craig, both of West Richland; Paul L. Reeder, Richland, all of Wash.

[73] Assignee: Battelle Memorial Institute, Richland, Wash.

[21] Appl. No.: 455,586

[22] Filed: May 31, 1995

[51] Int. Cl.[6] ................................................. A61N 5/00
[52] U.S. Cl. ........................................................ 600/1
[58] Field of Search ..................... 128/597–99; 600/1–8

Primary Examiner—John P. Lacyk
Attorney, Agent, or Firm—Johnnie R. Hynson; Paul W. Zimmerman

[57] ABSTRACT

The invention is a real time sensor for therapeutic radiation. A probe is placed in or near the patient that senses in real time the dose at the location of the probe. The strength of the dose is determined by either an insertion or an exit probe. The location is determined by a series of vertical and horizontal sensing elements that gives the operator a real time read out dose location relative to placement of the patient. The increased accuracy prevents serious tissue damage to the patient by preventing overdose or delivery of a dose to a wrong location within the body.

36 Claims, 7 Drawing Sheets

REAL TIME SENSOR FOR THERAPEUTIC RADIATION DELIVERY

This invention was made with Government support under Contract DE-AC06-76RLO 1830 awarded by the U. S. Department of Energy. The Government has certain rights to the invention.

FIELD OF THE INVENTION

The present invention relates generally to an apparatus for the determination of the location and amount of radiation dose and dose rate to a patient. More specifically to a probe for placement on, or insertion into, a patient to determine the exact location of the dose, and an element matrix to determine the location of that dose.

BACKGROUND OF THE INVENTION

Radiation is widely used for medical treatment. The primary radiation source is gamma or high energy x-rays. Thermal, epithermal, and high energy neutrons are also used.

It is critical that the amount and location of the radiation delivery be controlled as closely as possible. An error in intensity can either result in excessive tissue damage, or result in not accomplishing its intended purpose. An error in location can inadvertently cause damage to healthy tissue and organs, sometimes to critical organs such as eyes, brain, glands, etc, and cause severe debilitating damage and even death.

There are a number of sources of dose error, such as improperly calibrated sources, equipment malfunctions, and equipment deficiencies. Errors in calibration and equipment malfunctions can be prevented by quality checks and through properly implemented procedures. However, the equipment in use now can only function up to its maximum potential. The instant invention provides capabilities that were heretofore beyond the existing equipment's potential.

One method of estimating dose to a patient receiving thermal and epithermal neutron therapy is to insert a gold needle into the patient's cranium and then perform a partial exposure. The partial exposure is typically calculated to terminate at about the half-way point. The dose is generally terminated by the operator at the half-way point by turning off the source of radiation, or by closing off the radiation source. At that time the gold needle is removed and a radiation count is taken and dose calculations performed. The activation of the gold needle is assumed to be proportional to exposure to the gold needle. From the count rate taken on the gold needle the estimated dose received by the patient is calculated. Then the operator continues the radiation exposure to the full prescribed dosage. As is apparent the limitation of this method is that calculations themselves may be subject to error, there is no indication as to the exact location of the dose, and the calculation are based upon empirical calculations. Gold needles have a further limitation that it is not suitable for all types of radiation, and is particularly sensitive to certain energies and types of radiation. The energies and types of radiation may not be suitable for the detection of the particular types of radiation needed for the prescribed treatment.

Several different types of radiation detectors have been tried to solve these problems. However, these still do not solve the problems associated with inaccurate therapeutic radiation treatment.

For example, when using ionizing radiation a stimulated phosphor was used as a dose measure. Problems persisted because a laser or other infrared light source was needed to heat the active material to activate the excitations from the traps in the material. Since an infrared source is required, real-time measurement is not practical.

Another approach to achieving real-time measurement is the use of a phantom prior to irradiation. A phantom is in essence a model made of "equivalent material" to the object to be examined. The limitations on this method are obvious as it is the dose to the patient is needed, and this method is limited because the materials used in construction can only roughly simulate the human body.

Other attempts are limited in scope to only electromagnetic radiation. Non-electro-magnetic radiation, such as neutrons make up a significant portion of prescribed radiation doses.

The instant invention provides real time dose rate and location of all types of radiation being administered at this time, thus eliminating or reducing the errors that have taken a large toll in human damage.

SUMMARY OF THE INVENTION

The instant invention is an apparatus that allows a precise location and amount of dose to be read out in real time. This alerts the treatment provider to any error before further tissue damage is done to the patient. It also allows for real time dose and location to be controlled to an extent not achieved by the prior art.

Amount is determined by a probe inserted into, or placed near, the area to be treated. The probe is a scintillation detector constructed of doped scintillation fiber optic material that creates a light signal for the particular type of radiation to be used in treatment. For example, one probe can be used for high energy neutrons, and another for x-rays and gamma ray photons, and yet a third for thermal and epithermal neutrons. It is also contemplated that multipurpose probes can be used. An additional embodiment comprises a segmented probe to provide a more narrowly defined indication of the location of the radiation received by the patient.

The light signals from the probes are interpreted through standard equipment such as photo-multiplier tubes, solid-state detection devices, and multi-channel analyzers to provide the real time indications.

In another embodiment of the instant invention the location of the dose delivered to the patient is also determined by an element matrix of both horizontal and vertical sensing elements. The vertical axis runs substantially the length of the area to be treated, or alternately for the entire length of the patient. The horizontal axis runs the width of the area to be treated, or alternatively for the width of the patient. The intersection of a vertical sensing element and a horizontal sensing element indicates the location that the radiation strikes the element matrix. The relative position of the patient to the element matrix is easily used to calculate the impact point of the irradiation and the dose rate delivered to the patient to a high degree of accuracy and precision.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT(S)

Figure 1:
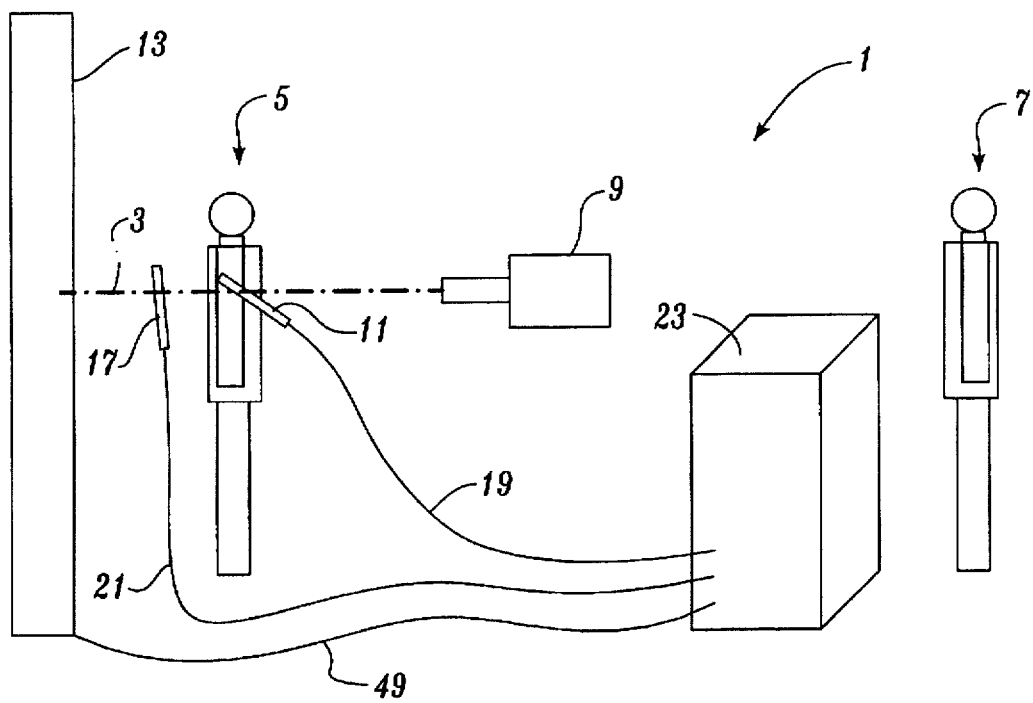
FIG. 1: Is a schematic representation of the real time dosimetry sensor illustrating the placement of a patient between the radiation beam and the location sensor, and further illustrating the use of the probe assembly.

The instant invention is a real time therapeutic radiation dosimetric sensor system 1 (RTTRDS) for controlling the therapeutic radiation 3 delivery to a patient 5. Referring to FIG. 1, an illustration of the RTTRDS 1 in use, the administration of a radiation dose 3 to a patient 5 is observed by an operator 7. Delivery of a prescribed radiation treatment requires the type of radiation 3 as well as both the dose and location of that radiation 3. Radiation is administered to the patient 5 by a radiation source 9. The radiation source 9 can be an x-ray machine, a gamma ray point source, a neutron point source or beam, or any number of fabricated or commercially available radiation sources. The RTTRDS 1 is capable of successful operation with any type of radiation 3 known at the present time.

PROBE ASSEMBLY

Figure 2:
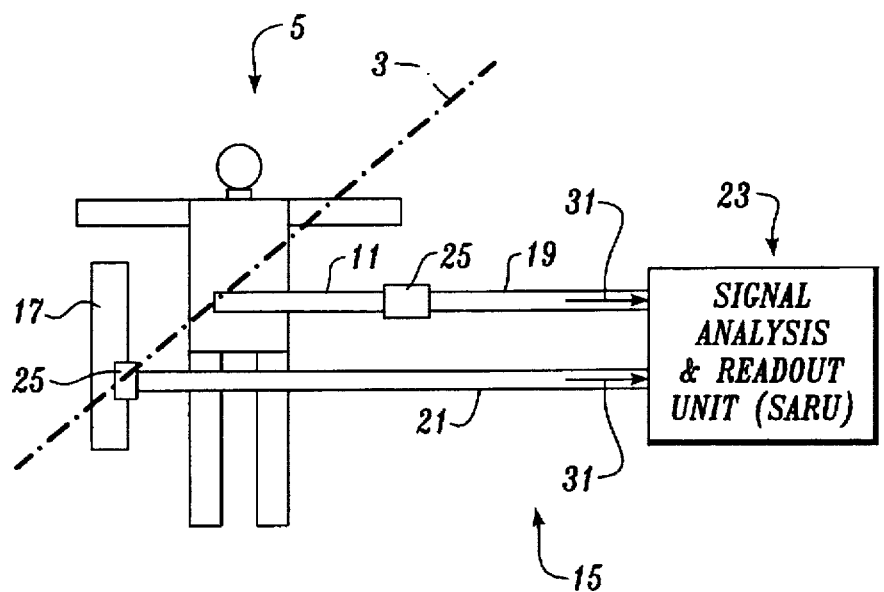
FIG. 2: Is a schematic representation of the probe assembly, illustrating the probe placed in a patient and the connecting cable and the signal analysis and readout unit (SARU).

Referring now to FIG. 2, the radiation 3 dose rate is measured by use of a probe assembly 15. The probe assembly 15 comprises at least one probe 11, an optional exit probe 17, a least one probe connecting cable 19, an optional exit probe connecting cable 21, and a signal analysis and readout unit (SARU) 23. The instant invention may be operated using only one probe which will be an insertion probe 11 (also referred to only as probe 11). The probe connecting cables 19,21 are typically a fiber optic cable that transmit the light signals 31 created by a detection event in the probe 11 to the SARU 23. It should be noted that in some instance it will not be necessary to place the probe within the patient. For example, in the treatment of cancer on the skin or close to the surface of the body.

Figure 3:
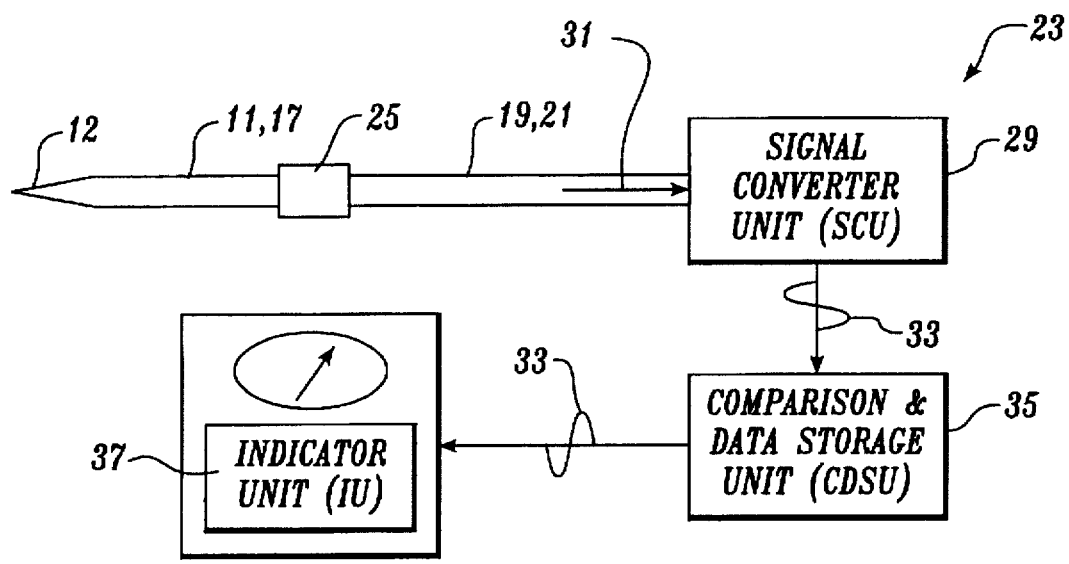
FIG. 3: Is a block diagram illustrating the components of the probe assembly and components used for signal analysis.

Referring to FIG. 3, if an optional signal convertor or amplifier 25 is used the probe connecting cables 19,21 will be an electrical cable. The insertion probe 11 is placed at or in the patient 5 at the location that the radiation 3 dose is to be administered. The insertion probe can have a sharp insertion end 12 to facilitate placement within the patient. Because scintillation material is difficult to grind or work, a sharpened point will have to be made on the probe coating 38, should one be desired. The when the probe is an exit probe 17 it would be placed at the point that radiation 3 exits from the patient.

The SARU 23 consists of a signal converter unit (SCU) 29, which is a means to convert light signals 31 to electrical signals 33 which are transmitted to a comparison and data storage unit (CDSU) 35. A single SARU 23 may be used for each probe that is used, or each probe may be fed into one SARU 23.

The light to electrical signal conversion is typically accomplished by a photomultiplier tube or a solid state device which makes up the SCU 29. From the CDSU 35, which are commercially available, the signal is sent to an indicator unit 37. The CDSU 35 typically consists of circuits to count the pulses received, compared to a preset-calibrated signal that is in storage within the unit and provides a signal that indicates the dose. The indicator unit (IU) 37 can be digital or a meter.

It is contemplated that for maximum utility and mobility all-electronic components be located within the SARU 23.

PROBE CONSTRUCTION

Figure 4A:
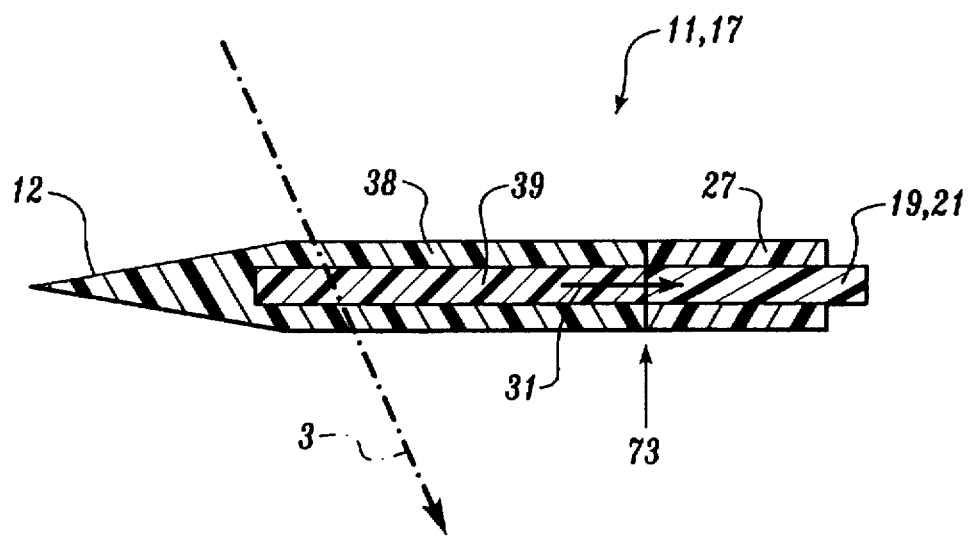
FIG. 4a: Is a cross-sectional representation of the internal construction of the probe illustrating the probe scintillator connection to a fiber optic cable.

Now referring to FIG. 4a an optical fiber connecting cable 19,21 that will typically have a flexible coating 27 is illustrated. Each probe 11,17 is provided with a coating 38 to minimize any interaction with the body of the patient 5. The type of coating of the probe should be selected for use in the prescribed radiation field. Polypropylene or polyethylene is recommended due to the low activation potential in radiation fields. Traditional materials, such as surgical steel, can become activated and cause additional problems. Actual insertion into the patient 5 is not required in all cases. An insertion requirement is more probable in practice of the instant invention in the cranial and thoracic cavities.

The radiation sensitive portion of the probe, the active portion 39, is constructed of fiber optic material doped to be reactive with the particular type of radiation 3 to be used during therapy.

It is contemplated that the insertion probe 11 and the exit probe 17 will be constructed in a similar manner. However, for economic reasons the exit probe 17 coating and the external shape can have less stringent requirements. However, for comparative calculations, required by use of the two probes, exact dimensions of the active portion 39 should be the same.

Insertion probes 11 will typically be shaped in a needle-like shape for ease of insertion into the patient 5. If the exit probes 17 are shaped in a needle-like shape then parallel alignment is necessary for the most accurate reading. If a different shaped exit probe 17 is used then an adjustment in the calculations will be necessary. The calculations can be adjusted by hand calculation or alternatively programmed into the circuitry.

PROBE SCINTILLATOR MATERIALS OF CONSTRUCTION

Referring again to FIG. 4a particular types of materials of construction are required to optimize the sensitivity to particular types of radiation 3. Both organic (such as plastic) and inorganic fibers can be used.

Thermal and Epithermal Neutrons

Epithermal neutrons are best detected with scintillator doped with $_3Li^6$. Another example would be lithium silicate glass doped with an activator ion such a light emitting $Ce^{+++}$ ion. Thermal neutrons are readily detected by this material as well. Cerium-activated $_3Li^6$-loaded glasses are fabricated by melting the raw materials under careful atmospheric control. The glass melt is quickly cooled by pouring onto a chilled metal plate. This glass can be made into a scintillating fiber form by remelting shards and drawing the fiber from the melt, coating the fresh fiber with an appropriate organic resin and polymerizing the resin on the fiber. Successful fabrication of neutron-sensitive scintillating glass is critically dependent upon control of the oxidation state during the glass melt and fiberizing processes.

Fast Neutrons

A radiation dose 3 of fast neutrons would be detectable by detecting the recoil protons using inorganic and organic scintillator materials.

Photons

When using the instant invention to detect the therapeutic dose of gammas and x-rays materials of the lowest possible Z number should be used to minimize the production of Compton electrons which can cause damage to the patient 5. A high Z number material can also cause broadening of flux profile with respect to distance in reference to the target areas, and should be avoided for that reason alone. Therefore, scintillator constructed of organic materials such as plastics are more adaptable for use with photons.

Segmentation of the Probe

Figure 4B:
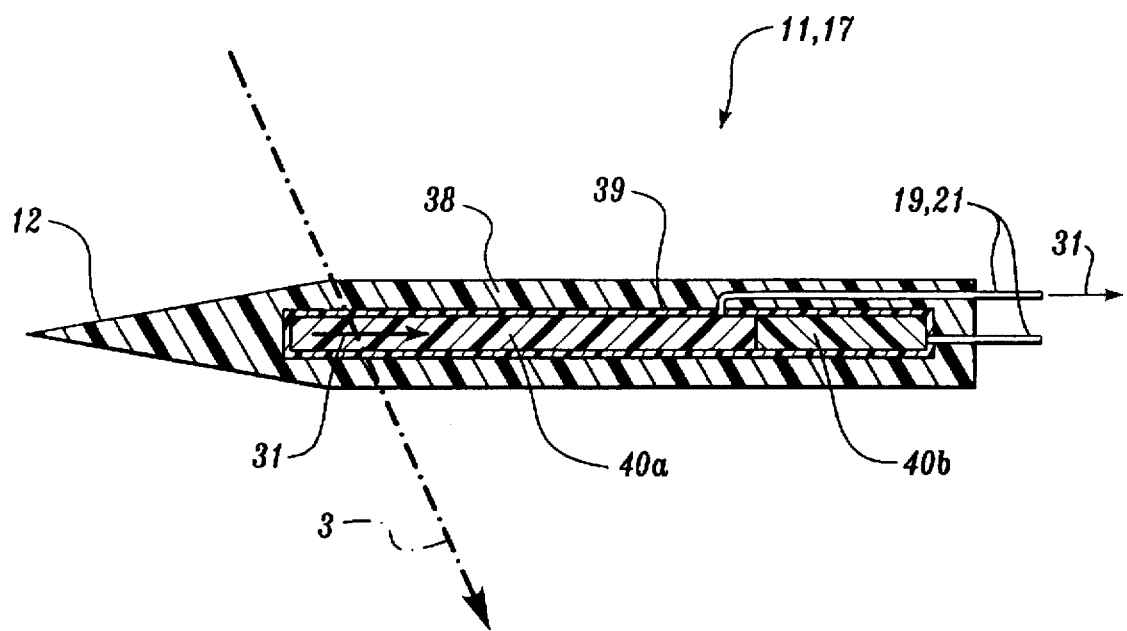
FIG. 4b: Is a cross-sectional representation of the internal construction of the probe illustrating a probe scintillator which has been segmented and connected to a fiber optic cable.

Now referring to FIG. 4b yet another embodiment comprises probe(s) 11,17 where the active portion 39 is segmented into segments 40a and 40b to provide a more narrowly defined indication of the radiation 3 location upon the patient 5 by being delineated into segments and each segment being read separately via connecting cables 19,21. The larger the number of segments such as 40a and 40b the higher the degree of accuracy that can be obtained.

The light signals 31 from the active portion 39, or segments 40, are interpreted through standard equipment such as photo-multiplier tubes, solid-state detectors, and multi-channel analyzers to provide the dose.

DOSE CALCULATION BY ABSORPTION

Figure 4C:
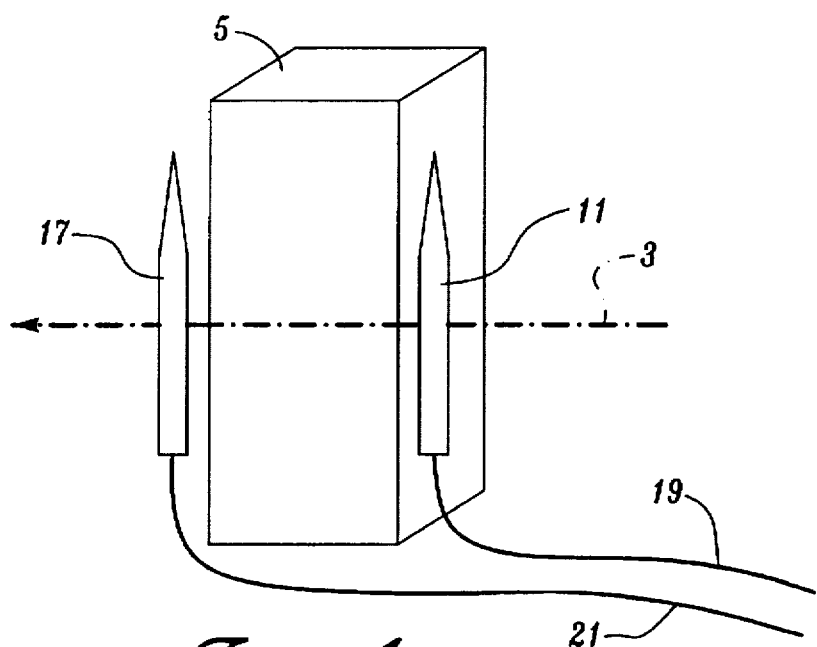
FIG. 4c: Is an isometric representation the placement of an exit probe and an insertion probe to calculate the dose absorbed by a patient.

Now referring to FIG. 4c an increase in accuracy in the actual dose absorbed by the patient 5 can also be calculated using an exit probe 17 (or element matrix 13). The difference in the radiation 3 dose rate at the insertion probe 11 and the exit probe 17 is directly related to the actual amount of dose absorbed by the patient's 5 tissues. The dose absorbed can be calculated by the following equation:

$$d_{abs} = d_{in} - d_{out}$$

where $d_{in}$ is the dose at the insertion probe, and where $d_{out}$ is the dose at the exit probe, and $d_{abs}$ is the dose absorbed by the patient 5.

ELEMENT MATRIX CONSTRUCTION

Figure 5A:
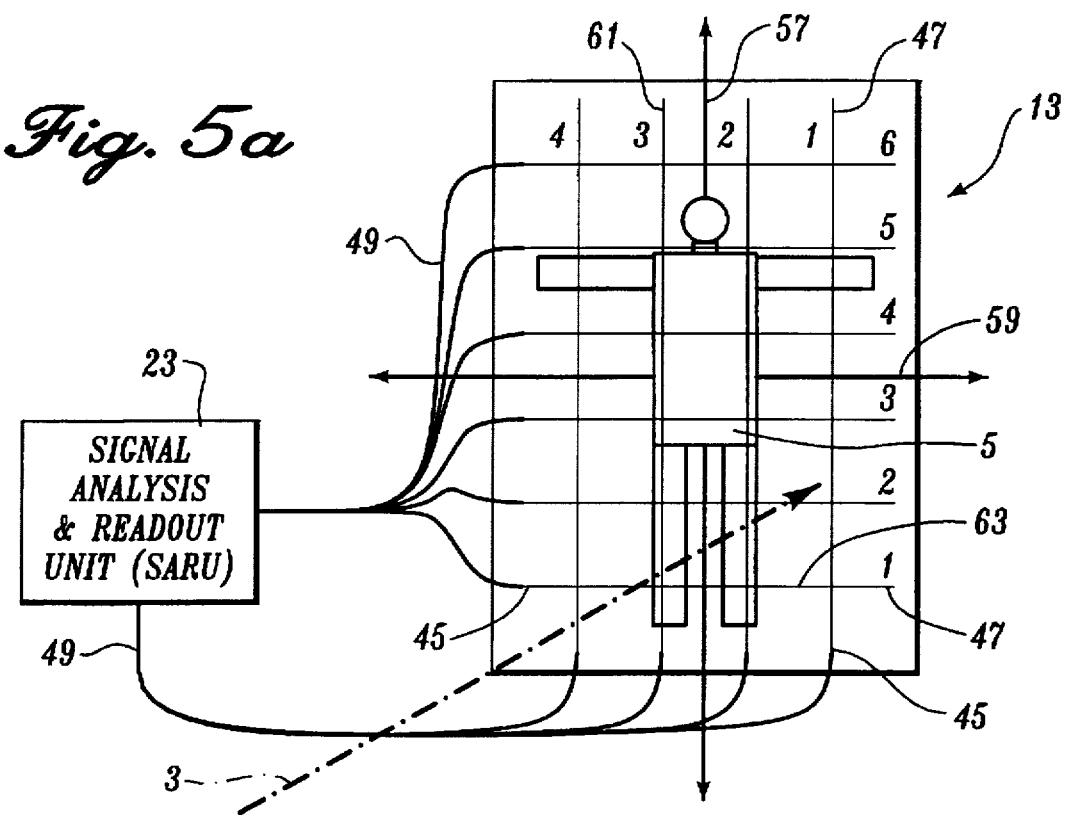
FIG. 5a: Is a schematic representation of a patient placed relative to an element matrix illustrating the connecting cable and the signal analysis device.

Now referring to FIG. 5a the location and magnitude of received radiation dose is determined by an element matrix 13 containing a plurality of horizontal sensing elements 63 and a plurality of vertical sensing elements 61. In this embodiment each of the sensing elements 61,63 have a free end 45 and a connecting end 47. The free end 47 determines the limit of the element matrix's 13 and the individual element's 61,63 ability to sense and measure radiation 3. The connecting end 45 of each sensing element is connected to a sensing element cable 49. The vertical sensing elements 61 and the horizontal sensing elements 63 are constructed of the same material as the active portion 39 as discussed above. The received light signals 31 are analyzed in the same manner as those received from the probes above.

Method of Determining Location

Referring now to FIG. 5a the vertical axis 57 runs substantially the length to the area to be treated, or alternately for the entire length of the patient 5. The horizontal axis 59 runs the width of the area to be treated, or alternatively for the width of the patient 5. The intersection of a particular vertical sensing element or strand 61 and a particular horizontal sensing element or strand 63 determines the location that the radiation 3 strikes the matrix element 13. The relative position of the patient 5 to the element matrix 13 is used to calculate the impact point of the radiation 3 on the patient 5 to a high degree of accuracy and precision.

A cartesian coordinate system readily lends itself to aid the location process. Referring again to FIG. 5a radiation 3 striking vertical sensing element 61 and horizontal sensing element 63 will define the location of the received dose as (1, 3). In FIG. 5a this will correspond to the patient's 5 right ankle 65. As in customary in the use of cartesian coordinates point (1, 3) refers to the horizontal sensing element numbered "1", and the vertical sensing element numbered "3".

Other Matrix Element Configurations

Figure 5B:
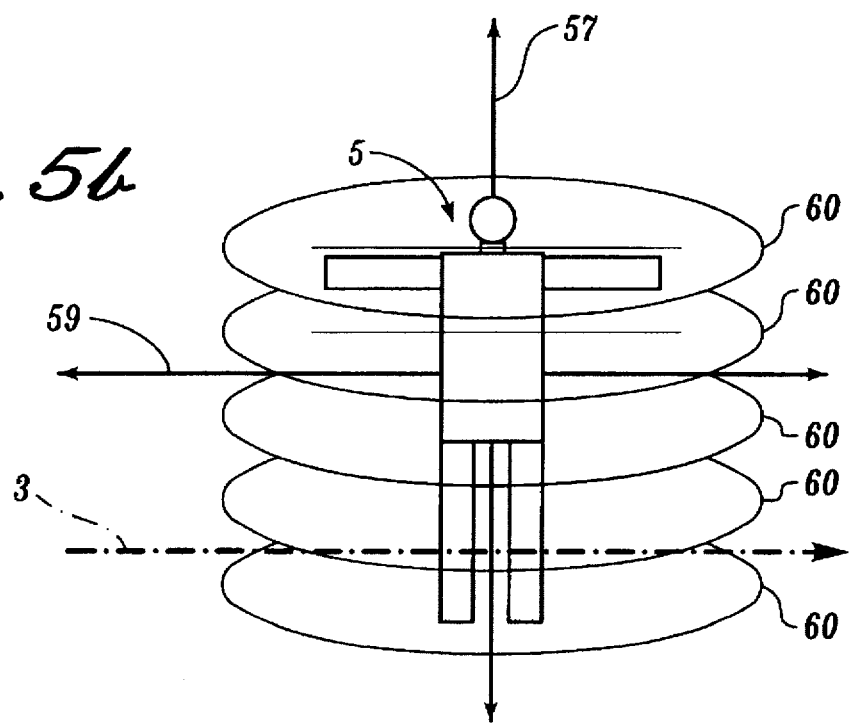
FIG. 5b: Is a schematic representation of a patient placed with an element matrix comprising of a series of rings.

Other coordination systems are within the contemplation of the practice of the instant invention. Referring now to FIG. 5b, for example, a series of horizontal ring elements 60 can be placed around the patient's 5 body, wherein the vertical location of dose administration can be indicated. Also more than one series of elements can be used at one time. For example, a series of vertical ring elements or horizontal ring elements s can be used in conjunction with a series of vertical or horizontal sensing elements.

Accuracy of Location Determination

While FIG. 5a illustrates elements at essentially 90° relative placement, any placement that provides sufficient resolution will work. The accuracy and precision achieved is dependent upon the number of vertical sensing elements 61 and horizontal sensing elements 63 used. The larger number of elements used, the higher degree of accuracy and precision can be achieved. Additionally, even the most narrowly collimated beam of radiation 3 will expand in size due to scattering as the beam penetrates the patient 5.

Elimination of Element Matrix Background Signal Noise

Figure 6A:
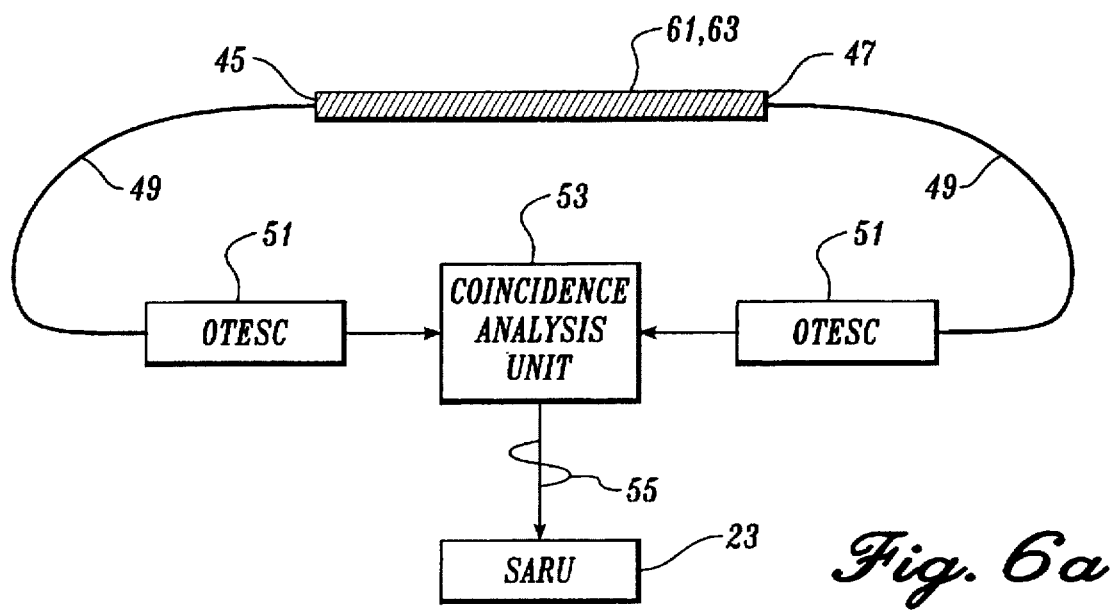
FIG. 6a: Is a schematic representation of the connection of each end of the vertical or horizontal elements to a coincidence analysis unit.

Now referring to FIG. 6a the vertical sensing elements 61 and the horizontal sensing elements 63 are connected by a sensing element cable 49 at each end 45,47 of each element 61,63. As with the probes discussed above the sensing element cable 49 will typically be constructed of fiber optic material to transmit the light signals 31 generated from a detection event. In this arrangement the light signal 31 produced by the horizontal sensing element 63 or the vertical sensing element 61 will be received simultaneously by an optical to electrical signal conversion unit (OTESCU) 51 from each end of the element. The electrical output from each OTESCU is then received by a coincidence analysis unit (CAU) 53. The output of the CAU 53 is an electrical or electronic signal 55 that is received by a SARU 23 as described above.

The CAU 53 separates system noise from desired signal and increases the accuracy and precision of the reading.

High Resolution Dose Location Determination

Figure 6B:
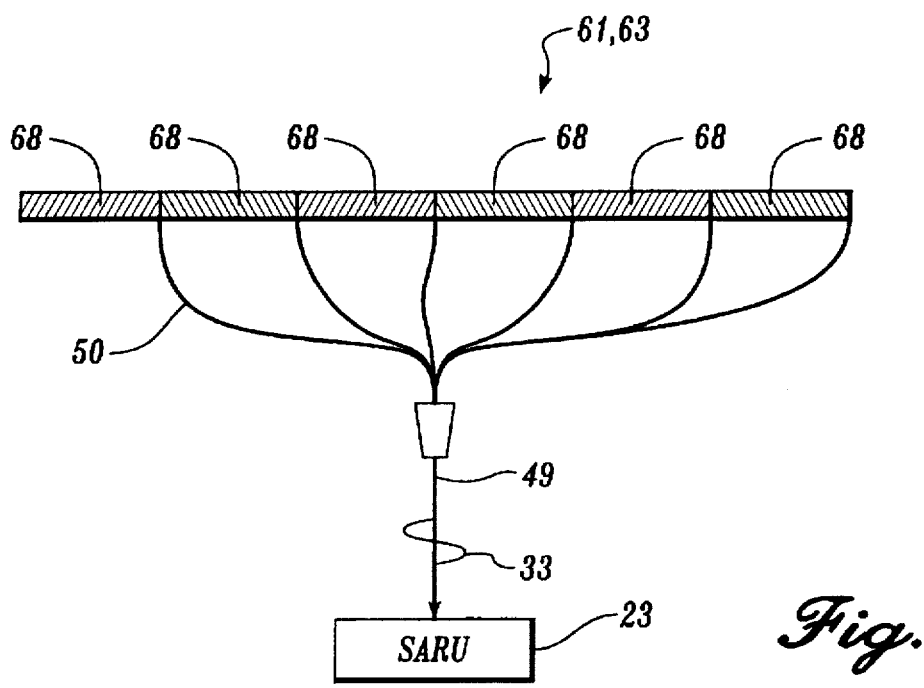
FIG. 6b: Is a schematic representation of a segmented sensing element.

Referring now to FIG. 6b, with each vertical sensing element 61 and horizontal sensing element 63 providing a light signal 31 into a connecting cable 49 which is read by the SARU 23 only the average over the length of that sensing element 61,63 will be determined. Therefore in cases where an increase in precision is desired, the sensing elements 61,63 may be segmented into segments 68. Each of these segments 68 can be received separately by the SARU 23 via segment cables 50. Therefore, an increase in resolution is possible because the location of highest signal strength along the length of a single segment 68 can be determined. The length of the segment can be shortened to a point source or can be as large as a major portion of the length of a single sensing element 61,63. As with a full sensing element 61,63 each end of a segment 68 may be attached to a cable.

Figure 6C:
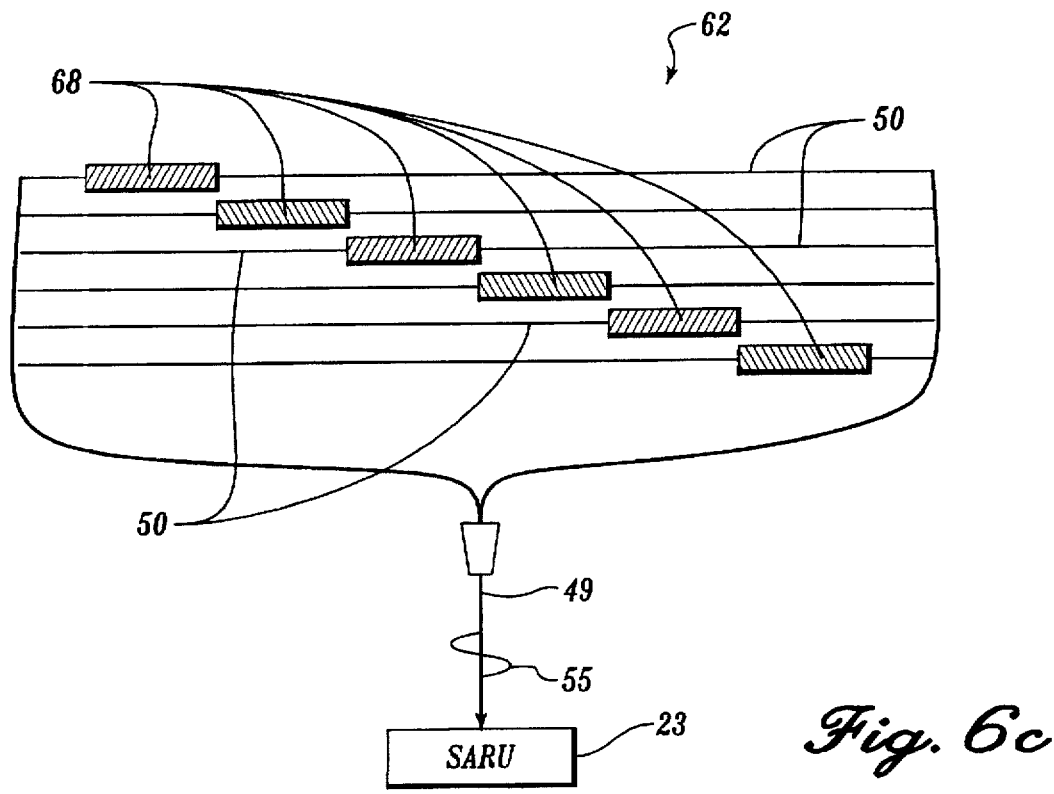
FIG. 6c: Is a schematic representation of a segmented sensing element pattern.

FIG. 6c illustrates an embodiment wherein segments are placed in a segment pattern 62 that will embody both high resolution and ease of assembly. The segments 68 would typically be aligned to a straight row for ease of assembly in the matrix. Accordingly, in this embodiment, a vertical sensing element 61 or a horizontal sensing element 63 would be a string of segments 68 placed end to end. In this embodiment light signals 31 can be received for one end, as in with a probe 11,17; or both ends of the segment simultaneously, and used with a coincidence circuitry as described above.

In another embodiment of the instant invention the bundle of optical fibers will be approximately 100 micrometers in diameter and 0.5 cm in width.

DOSE DETERMINATION TO SURROUNDING TISSUES

Figure 7A:
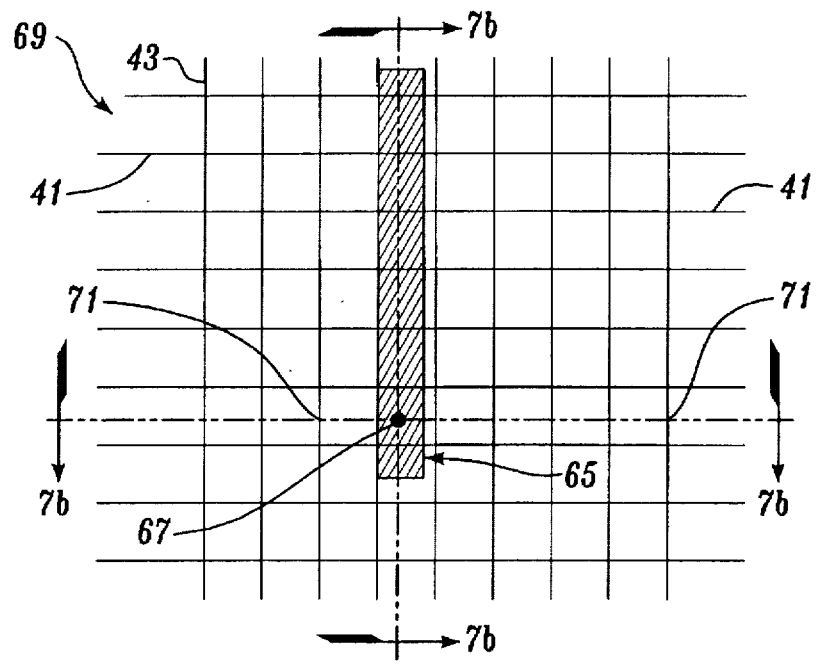
FIG. 7a: Is a top view of a patient's ankle receiving a dose relative to a matrix of vertical and horizontal sensing elements.
Figure 7B:
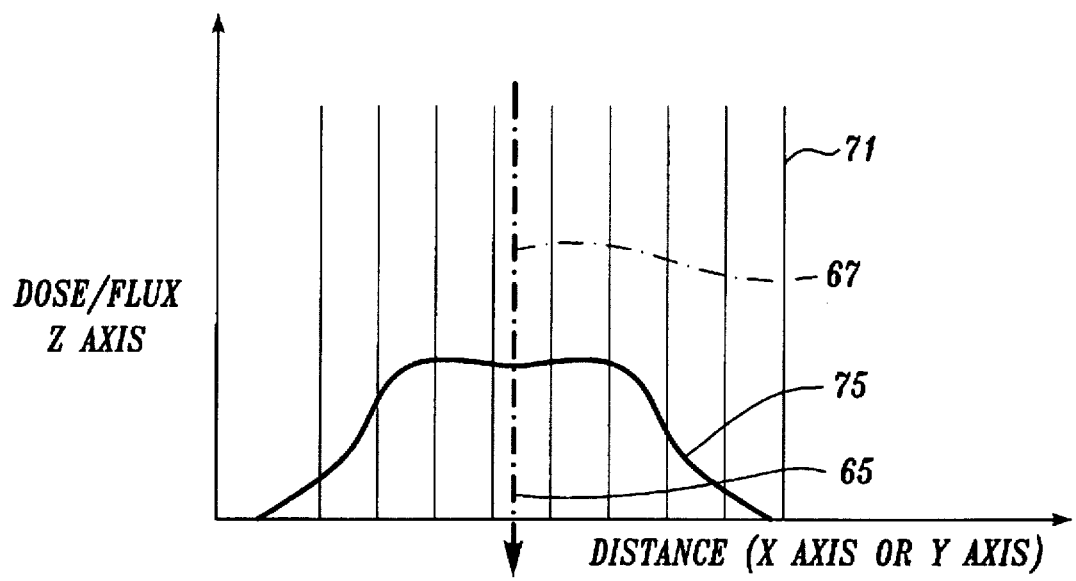
FIG. 7b: Is a side view of the radiation flux profile along lines 7b—7b.

Referring now to FIGS. 7a and 7b, it is often desirous to know the dose to tissues surrounding the area to be treated. By cross-correlations of the dose rate and location of that dose rate a radiation profile 75 can be determined.

FIG. 7a is an illustration of a collimated dose 67 to the patent's right ankle 65 viewed relative to a portion of the grid 69 of horizontal sensing elements 63 and vertical sensing elements 61. Please note that the vertical axis (which is the axis of the vertical sensing elements 61) is considered the Y axis, and that the horizontal axis (which is the axis of the horizontal sensing elements 63) is considered the X axis.

When the collimated beam of radiation 67 is administered to the patient's right ankle 65 the radiation will then scatter and create a radiation flux strength vs. position pattern as illustrated in FIG. 7b. The dose rate at each position on the X-Y plane can be determined by measuring the signal strength in both the vertical or horizontal element indicating that position. FIG. 7b is a two-dimensional representation of a three dimensional graph 75 along the center of the ankle 65 illustrating a correspondence to intersection points 71. The vertical displacement on FIG. 7b is the Z axis and represents dose received. The higher the dose received at that point the graph at that point on the X-Y plane. Please note for FIGS. 7a and 7b a symmetrical distribution of radiation from scattering of the collimated dose 67 is assumed. In actual practice this would only be true if the structures being treated within the patient are homogenous over the range of investigation, which is highly unlikely.

In 3-dimensional space the dose received would appear as a flattened cone, with the center of the cone being the center of the collimated dose 67, and assuming that the collimated dose in administer perpendicularly to the X-Y plane. The vertical axis referred to in FIG. 7b is the dose strength in the vertical or Z axis.

SIGNAL ANALYSIS AND READOUT UNIT

The construction of SARU 23 can take several different forms. The light signal 31 created in the probes 11,17, and the element matrix 13 are transmitted via the connecting cables 19,21 for the probes and will typically be received by a SCU 29, such as a photo-multiplier tube, or a solid-state detector, which produces electrical signals 33. The electrical signals 33 can be read and analyzed by a number of commercially or custom made devices. Typically, a multi-channel analyzer (not shown) is used to determine the precise energy of the radiation 3 received versus number of events detected at each energy.

Insertion Probe Signal Analysis: A first analysis is to determine the dose rate of the radiation 3 striking the probe. Through standard calibration techniques the number of events in the probes can be calculated by the SARU 23 to determine the actual dose to the probe at that point within or on the patient 5.

Commercially available digital display or meters can be used to read the actual dose in real time by the operator 7.

Comparison of Probe Signals: The difference in dose rates between the insertion probe 11 and the exit probe 17 can give a very precise determination of the dose rate between the two probes. Circuitry is commercially available to make this comparison.

Matrix Signal Analysis: The second analysis is to be able to read the relative location of the dose that is received by the patient 5. By knowing the position of the patient 5 relative to the element matrix 13 the actual location that the dose strikes the patient 5 is readily calculable.

Remote Signal Conversion or Amplification: There is a signal transmission limitation with distance in the current state of art in fiber optics. It is therefore contemplated to be within the practice of the instant invention that a light signal convertor and/or amplification device 25 be placed at the end of the active portion 39, vertical sensing element 61, or horizontal sensing element 63 to increase signal strength received at the SARU 23. Similarly, the signal can be converted to electrical impulses and transmitted from there to the signal analysis and readout unit 23, with or without amplification.

Calibration: The calibration relating the optical pulse generation rate of dose 3 to the patient 5 can be achieved through the use of calculations based on the properties of the active portion of the sensing elements or probe. This calibration can be checked through the use of phantoms to simulate the composition of the body. Suitable materials exist which can be activated by the radiation (for instance, but not restricted to, LiF for electromagnetic radiation or gold wires for thermal/epithermal neutron radiation) to measure the actual radiation dose delivered to the phantom. Use of phantoms and gold wires is known in the art.

Calibration of the particular probe or sensing element can be achieved by placing the detector into a known flux and the signals generated within the instant invention measured; then, a factor can be entered into the circuitry used to account for the measured variation in performance of the detector from that of other detection assemblies. In the practice of the instant invention, all available methods of calibration can be used, as appropriate, to provide cross checks and the highest possible accuracy.

DETERMINATION OF LOCATION BY PULSE HEIGHT

Figure 8:
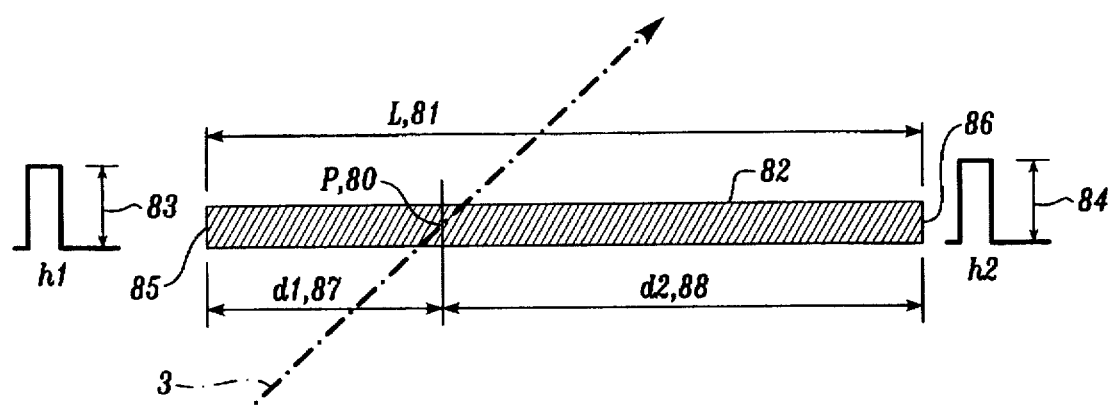
FIG. 8: Is a schematic representation of a segment of sensing element illustrating the pulse height received at each end when a radiation detection event occurs at a location other than the center.

Now referring to FIG. 8 it is possible to determine the radiation flux 3 at point P,80 within a length of sensing elements 61,63 of given length L,81 of a segment of sensing element 82 by using an analysis of the pulse heights h1,83 and h2,84 at segment ends 85,86. Point P,80 is the point that radiation 3 strikes the segment of sensing element 82. The same procedure is applicable to a length of probe 11,17.

This is done by measuring the pulse height h1,83 at the first segment end 85 of the segment of sensing element 82, of a pulse originating from point P,80 that is a distance d1,87 from that first segment end 85. Pulse height h1,83 decreases in substantially an exponential way with the distance d1,87 from the point of interaction P,80.

The pulse height h1,83 is compared to that of the pulse height h2,84 that is received at the second segment end 86 of the segment of sensing element 82 that must travel a distance of d2,88.

The distances d1,87 and d2,88 are calculated from the differences in pulse heights expressed as [(h1,83)−(h2,84)]. It should be noted that L,81 is always equal to [(d1,87)+ (d2,88)].

RESOLVING PROBE SCINTILLATOR-CONNECTING CABLE INTERFACE PROBLEMS

The organic or inorganic optical fibers used in the instant invention are capable of transmitting light signals 31 over long distances. The physical basis for this ability is the phenomenon of total internal reflection. The successful practice of the fiber optic cable embodiment of the instant invention necessitates an interface 73 between the active portion 39 and a connecting optical fiber cable 19,21.

Total internal reflection of electromagnetic radiation occurs at an interface 73 when two conditions are met: 1) the refractive index of the material onto which the light is incident is smaller than that of the material from which the light is coming and 2) the angle of the light ray is smaller than some angle which is determined by the two refractive indices. When these two conditions are met in a waveguiding geometry, i.e., the refractive index of the core is greater than that of the cladding, the radiation will propagate with loss only determined by the absorptive properties of the two materials.

Light signals 31 are generated isotopically inside the active portion 39. Light signals 31 generated and meeting the conditions for total internal reflection will be trapped within the fiber and carried towards either end of the active portion 39, particularly toward the interface edge 73 between the active portion 39 and the connecting cable. For light emitted on the axis of the fiber, the totally internally reflected rays make up a cone of light signal with its center coinciding with the axis of the fiber; for light emitted off the axis, the captured light includes rays whose trajectory is screw-like down the fiber.

At the probe scintillator-connecting cable interface 73 the light will either enter the connecting cable or be reflected at the interface 73. The reflection is minimized when the difference between the refractive indices of the two fiber cores is minimized and when the quality of the interface is maximized. The light signal 31 entering the connecting cable 39 will be transmitted without reflective loss only if the ray angles in the second fiber meet the condition for total internal reflection. Therefore, it is important to the successful practice of the invention that the refractive indices of the optical fibers of the active portion 39 and the connecting cable 49 be properly matched.

OTHER EMBODIMENTS

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. An apparatus for determining the relative dose rate of a therapeutic radiation received by a patient, comprising:
   (a) a probe assembly comprising:
      (i) at least one probe for placement near on internal to the patient, said probe having
         a coating,
         an insertion end and an attaching end,
         an active portion within said probe constructed of a scintillation material, said scintillation material producing a signal upon being exposed to said therapeutic radiation;
      (ii) a probe connecting cable, having a first end and a second end,
         a signal analysis and readout unit connected to said probe with said probe connecting cable connected to a first electronic port of the signal analysis and readout unit;
      (iii) said attaching end attached to said first end;
      (iv) said second end being attached to the signal analysis and readout unit,
         said signal analysis and readout unit receiving signals from said scintillation material via said probe connecting cable, said signal analysis and readout unit having a signal detection and calculation means therein;
   wherein said signal and analysis unit determines said relative dose rate that is indicated on the signal analysis and readout unit, and is representative of the radiation dose received at the location of said probe.

2. The apparatus as recited in claim 1, further comprising:
   (b) a location assembly comprising:
      (i) an element matrix comprising a plurality of vertical sensing elements and a plurality of horizontal sensing elements;
      (ii) said vertical and horizontal sensing elements each constructed of scintillator material, each of said horizontal and vertical sensing elements having an assembly end and a free end;

(iii) an element matrix connecting cable, having a first end and a second end;

(iv) said assembly end attached to said first end;

(v) said second end being attached to a second electronic port of the signal analysis and readout unit, said signal analysis and readout unit receiving signals from said scintillation material via said element matrix connecting cable, said signal analysis and readout unit having a signal detection and calculation means therein;

wherein when said patient is placed in a known relative position to said element matrix said signal analysis unit indicated the relative location of said radiation dose.

3. The apparatus in claim 1 wherein the radiation dose is selected from the group comprising: thermal neutrons, epithermal neutrons, fast neutrons, gamma rays, or x-rays.

4. The apparatus in claim 1 wherein said probe assembly comprises an insertion probe and an exit probe, whereby the radiation dose rate is determined by the radiation dose difference between the two probes.

5. The apparatus in claim 1 wherein the signal analysis and readout unit comprises a solid state optical detector and a comparison and data storage unit which receives electrical signals from the solid state optical detector, and an indicator unit which receives electrical signals from the comparison and data storage unit and indicates the dose and relative location received by the patient.

6. The apparatus in claim 5 wherein the optical detector is a photo-multiplier tube.

7. The apparatus in claim 5 wherein the readout device is an analog indicator.

8. The apparatus in claim 5 wherein the readout device is a digital indicator.

9. The apparatus in claim 1 wherein the active portion is constructed of an organic fiber optic material.

10. The apparatus in claim 1 wherein organic fiber optic material is plastic.

11. The apparatus in claim 1 wherein the active portion is constructed of an inorganic fiber optic material.

12. The apparatus in claim 11 wherein the active portion is constructed of a fiber optic glass doped with a dopant.

13. The apparatus in claim 12 wherein the dopant is $_3Li^6$.

14. The apparatus in claim 9 wherein the active portion is constructed of a fiber optic glass doped with a light-emitting activator ion.

15. The apparatus in claim 14 wherein the activator ion is $Ce^{3+}$.

16. The apparatus in claim 2 wherein the sensing elements are constructed of an organic fiber optic material.

17. The apparatus in claim 1 wherein the organic fiber optic material is plastic.

18. The apparatus in claim 2 wherein the sensing elements are constructed of an inorganic fiber optic material.

19. The apparatus in claim 17 wherein the sensing elements are constructed of a fiber optic glass doped with a dopant.

20. The apparatus in claim 19 wherein the dopant is $_3Li^6$.

21. The apparatus in claim 2 wherein the vertical sensing elements and the horizontal sensing elements are substantially at right angles.

22. The apparatus in claim 2 wherein the vertical sensing elements and the horizontal sensing elements are substantially at an acute angle.

23. The apparatus in claim 2 wherein the element matrix is a series of ring elements.

24. The apparatus in claim 2 wherein the element matrix is a series of ring elements used concurrently with a series of vertical sensing elements.

25. The apparatus in claim 2 wherein the element matrix is a series of ring elements concurrently with a series of horizontal sensing elements.

26. The apparatus in claim 2 wherein said sensing elements are segmented into portions, each segment connected by a connecting cable to the signal and analysis and readout unit.

27. The apparatus in claim 1 wherein the connecting cables are constructed of an organic fiber optic material.

28. The apparatus in claim 1 wherein the organic fiber optic material is plastic.

29. The apparatus in claim 1 wherein the connecting cables are constructed of an inorganic fiber optic material.

30. The apparatus in claim 26 wherein the connecting cables are constructed of a fiber optic glass doped with a dopant.

31. The apparatus in claim 30 wherein the dopant is $_3Li^6$.

32. The apparatus in claim 1 wherein the connecting cables are constructed of an electrical conductor.

33. The apparatus in claim 1 wherein background signal noise is reduced by means of a coincidence analysis unit.

34. An apparatus for determining the relative location and dose rate of therapeutic radiation received by a patient, comprising:

(a) a probe assembly comprising;
   (i) at least one probe placed in the vicinity of the patient, said probe having
       a coating on said probe,
       an insertion end and an attaching end, and
       an active portion constructed of a scintillation material;
   (ii) a probe connecting cable, having a first end and a second end;
   (iii) said attaching end attached to said first end;
   (iv) a signal and analysis readout unit attached to said second end;
   wherein said radiation dose rate is determined and indicated on the signal analysis and readout unit;

(b) a location assembly comprising:
   (i) an element matrix of a plurality of vertical sensing elements and a plurality of horizontal sensing elements;
   (ii) said vertical and horizontal sensing elements each constructed of scintillator material,
   (iii) said horizontal and vertical sensing elements having a first assembly end and a second assembly end;
   (iii) a plurality of element matrix connecting cables, having a first end and a second end;
   (iv) a signal analysis and readout unit connected to said probe with said second end being attached to the signal analysis and readout unit;
   (v) said second end of said plurality being attached to a coincidence analysis unit;
   (vi) said coincidence analysis unit emits and electrical signal only upon a confirmed detection event occurring in said sensing elements, said electrical signal being received by the signal analysis and readout unit;

wherein when said patient is placed relative to said element matrix said signal analysis unit indicates the relative location of said radiation dose.

35. The apparatus in claim 1 wherein the location of a radiation flux interaction along the vertical sensing element and horizontal sensing element is determined by:

measuring a first pulse height h1 received at a first segment end, measuring a second pulse height h2 received at a second segment end, the difference in said pulse heights indicating;
   a distance d1 from one segment end, and
   a distance d2 from said second segment end.

36. The apparatus in claim 1 wherein the location of a radiation flux interaction along the probe is determined by:
   measuring a first pulse height h1 received at a first segment end,
   measuring a second pulse height h2 received at a second segment end,
   the difference in said pulse heights indicating;
      a distance d1 from one segment end, and
      a distance d2 from said second segment end.

* * * * *